United States Patent [19]
Drobish et al.

[11] 3,991,760
[45] Nov. 16, 1976

[54] VAGINAL MEDICAMENT DISPENSING MEANS

[75] Inventors: James Lee Drobish, Wyoming; Thomas William Gougeon, Cincinnati, both of Ohio

[73] Assignee: The Procter & Gamble Company, Cincinnati, Ohio

[22] Filed: Dec. 2, 1975

[21] Appl. No.: 636,898

[52] U.S. Cl. ............................. 128/260; 128/127; 128/129
[51] Int. Cl.² ..................... A61M 31/00; A61F 5/46
[58] Field of Search ........... 128/127, 130, 272, 129, 128/260

[56] References Cited
UNITED STATES PATENTS

| | | |
|---|---|---|
| 2,856,920 | 10/1958 | Indelicato ........................ 128/130 |
| 3,095,877 | 7/1963 | Rowan ............................. 128/260 |
| 3,200,815 | 8/1965 | Margulies ......................... 128/130 |
| 3,405,711 | 10/1968 | Bakunin ........................... 128/130 |
| 3,444,858 | 5/1969 | Russell ............................ 128/260 |
| 3,545,439 | 12/1970 | Duncan ............................ 128/260 |
| 3,867,933 | 2/1975 | Kitrilaskis ....................... 128/129 |

*Primary Examiner*—Aldrich F. Medbery
*Attorney, Agent, or Firm*—Richard C. Witte; Julius P. Filcik; Jerry J. Yetter

[57] ABSTRACT

Improved dispensing means for medicaments, contraceptives, and the like, which can be retained in the vagina during intercourse are provided.

12 Claims, 6 Drawing Figures

VAGINAL MEDICAMENT DISPENSING MEANS

BACKGROUND OF THE INVENTION

The present invention encompasses articles which are used in the vagina to deliver biologically active agents, especially contraceptives. By virtue of their unique construction and resulting shape, the articles remain in position, even during intercourse, so that delivery of the biologically active agent is not interrupted.

The articles of this invention are designed for use in the vagina, can be inserted by the user, and do not require fitting by a physician as, for example, in the case of intrauterine contraceptive devices. The articles are designed to remain in the vagina during the time between menstrual periods to provide desirable, prolonged release of a biologically active agent, and their construction and shape facilitate retention therein. It will be appreciated that when the biologically active agent is a contraceptive, an effective between-period contraceptive device is provided.

The copending application of Robert G. Laughlin, entitled CONTROLLED RELEASE ARTICLE, Ser. No. 560,020, filed Mar. 19, 1975, describes "controlled release" articles which are especially useful as contraceptives. By the present invention, articles operating by the controlled release mechanism described by Laughlin are constructed in such manner and configuration that said articles can be worn continuously during the period between menses and can be left in place in the vagina during intercourse. The unique construction obviates the need for removal and re-insertion and allows uninterrupted delivery of the contraceptive agent. The construction and shape also promote retention deep within the vaginal cavity, a position which favors contraceptive efficacy and wearing comfort.

Lichtman, et al., *Contraception* 8(4) 291-7 (1973), the disclosures of which are incorporated herein by reference, describe a vaginal contraceptive device comprising a soluble film containing a nonionic surfactant as a spermicide. Such devices can also be fashioned from slow-dissolving films into shapes corresponding to the articles herein so that they can be retained in the vagina during intercourse.

A series of patents relating to drug delivery, especially to the area surrounding the eye, describe various means whereby medicaments and the like can be enclosed within permeable membranes to yield so-called "sustained release" devices. See, for example, U.S. Pat. No. 3,828,777 MICROPOROUS OCULAR DEVICE, issued Aug. 13, 1974 to R. A. Ness; U.S. Pat. No. 3,618,604 OCULAR INSERT, issued Nov. 9, 1971 to R. A. Ness; U.S. Pat. No. 3,416,530 EYEBALL MEDICATION DISPENSING TABLET, issued Dec. 17, 1968 to R. A. Ness; U.S. Pat. No. 3,832,252 METHOD OF MAKING A DRUG DELIVERY DEVICE, issued Aug. 27, 1974 to T. Higuchi and H. M. Lieper (see also U.S. Pat. No. 3,598,122, issued 10/1971, other references cited in Higuchi, et al., as well as U.S. Pat. No. 3,867,519) the disclosures of said patents being incorporated herein by reference. Following the practice of this invention, the devices described in the foregoing patents can all be fashioned into articles of the present type, thereby allowing prolonged release of various desirable medicaments, and the like, into the vaginal area, which are comfortably worn and dependably retained even during intercourse.

The concurrently-filed application of Gougeon, entitled DISPENSING MEANS, Ser. No. 636,899, filed 12-02-75, also relates to vaginal contraceptives, and the like, constructed in a manner so as to be vaginally-retainable.

The concurrently-filed application of Drobish, entitled DISPENSING MEANS, Ser. No. 636,897, filed 12-02-75, also relates to vaginal contraceptives, and the like, constructed in a manner so as to be vaginally-retainable.

The copending application of Hughes, Ser. No. 578,297, filed May 16, 1975, relates to shaped vaginal contraceptives, and the like.

SUMMARY OF THE INVENTION

The present invention combines the desirable features of articles which provide prolonged release of a biologically active agent, e.g., a medicament, spermicide, or the like, into the vaginal area with the added advantages that the unique construction and shape of the present articles allows them to be worn comfortably in the vagina for periods of several weeks and to remain substantially undisturbed within the vaginal cavity during sexual intercourse.

As can be seen by reference to the Figures herein, the present articles for use within the vaginal cavity are characterized by a plurality of containers, said containers releasably containing a biologically active agent, said containers being connected by a thin, flexible seal fin in the plane perpendicular to the plane of the article. By virtue of the seal fin, the containers are disposed in such manner as to provide points of abutment between adjacent, filled containers, thereby holding said article in the desired, substantially circular configuration (i.e., the article is toroidal).

The articles herein are especially useful as contraceptives. Preferred contraceptive articles herein operate by the controlled release mechanism as described hereinafter and as more fully described in the copending application of Laughlin, above, the disclosures of which are incorporated herein by reference. Briefly stated, such preferred articles make use of the association colloid nature of certain spermicidal surfactants to provide, in combination with a semi-permeable membrane, a reservoir of spermicide within a controlled release article. Surfactant monomers migrate through properly selected membranes in a controlled fashion to provide a contraceptive effect for 20–30 days.

While the novel features of the present articles are perhaps best appreciated when considering their use as controlled release vaginal contraceptives, it will be understood that similarly constructed articles can be used to deliver all types of desirable medicaments and, by virtue of their construction and shape, are easily positioned in the vagina, are retained therein, can remain in the vagina during intercourse, and can remain therein for many days without discomfort or without even being noticed by the average user.

The present articles are prepared from components which are described in detail hereinafter.

The wall of a container 11 is cut away to show liquid 50, which is a solution of the biologically active agent herein.

Figure 2:
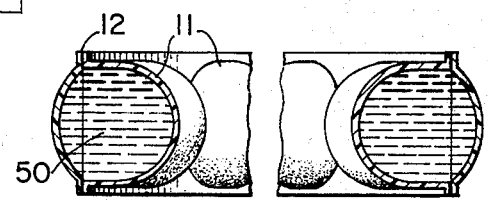

FIG. 2 is a section view of the article 10, showing the containers 11, liquid 50, and the relationship of the seal fin 12 to the containers.

Figure 3:
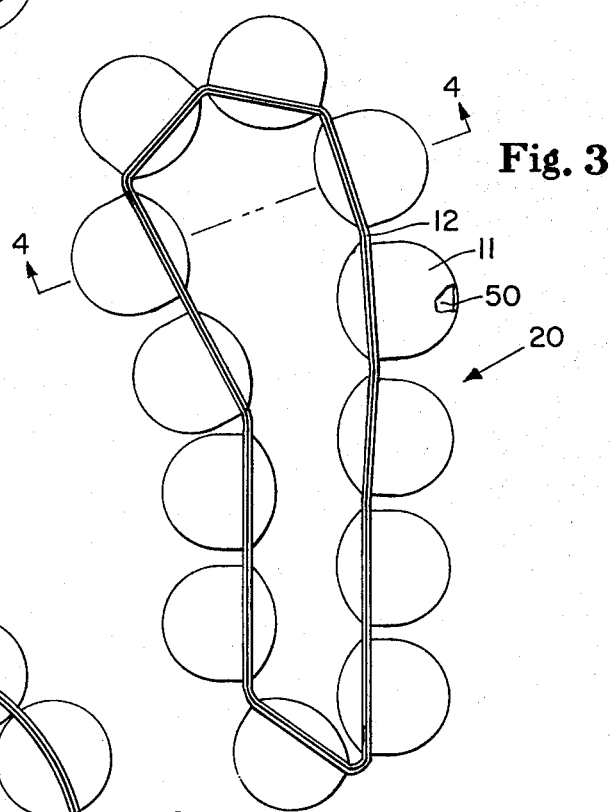

FIG. 3 is a plan view of an article 20 which is not retained in the vaginal cavity in optimal fashion. Article 20 comprises multiple, substantially spherical containers 11, liquid 50, and seal fin 12 in the plane substantially perpendicular to the plane of the article. However, the seal fin and containers are so disposed that there is substantially no abutment between the containers, and the article 20 is limp.

Figure 4:
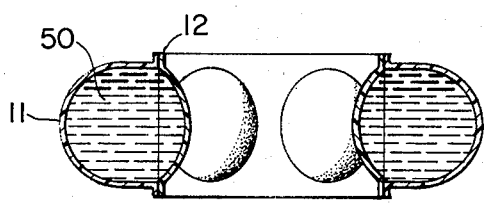

FIG. 4 is a section view of article 20 showing the relationship of the containers 11 (with liquid 50) and seal fin 12.

Figure 5:
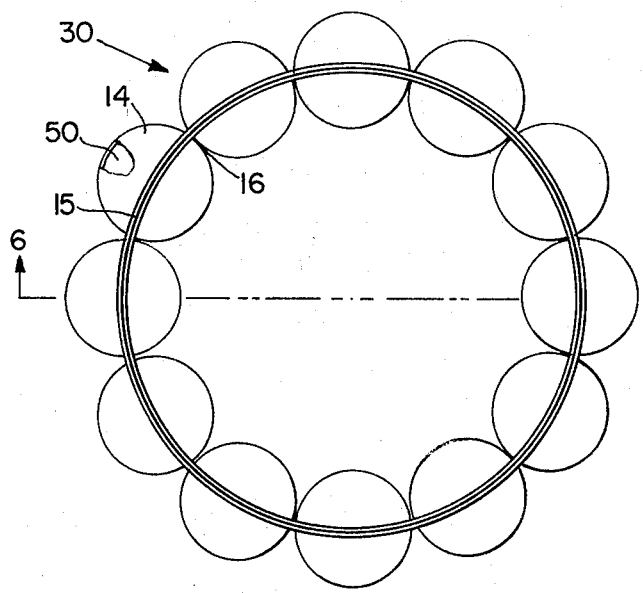

FIG. 5 is a plan view of an article 30 having substantially spherical containers 14, liquid 50, seal fin 15 in the plane substantially perpendicular to the plane of the article, and multiple points of abutment 16, which hold the otherwise flexible article in a substantially circular configuration.

Figure 6:
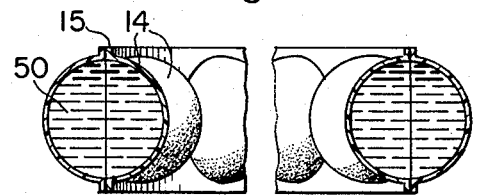

FIG. 6 is a section view of the article of FIG. 5 showing containers 14, liquid 50 and seal fin 15.

DETAILED DESCRIPTION OF THE INVENTION

By the present invention, an article which delivers metered doses of biologically active agents, especially contraceptive surfactants, to the vaginal cavity is constructed in a manner which provides a shape whereby said article can remain in the vagina during intercourse.

The desirability of providing metered dosage forms of biologically active or medicinal agents has long been recognized. Metered dosages can be manifest either as "controlled release" or "sustained release" of a given material. The distinction between controlled release and sustained or prolonged release has been recognized; see Cowsar, in "Advances in Experimental Medicine and Biology," Vol. 49, "Controlled Release of Biologically Active Agents," Ed. Tanquary and Lacey, Plenum Press, New York 1974.

Briefly stated, controlled release articles respond rapidly to changes such as dilution effects in the environment external to the article, e.g., by body fluid changes, whereas sustained release articles do not. The net result is that articles based on the principle of controlled release are capable of rapidly establishing an effective level or concentration of a medicament or other agent in a selected environment, and then substantially shutting off release so as to maintain the concentration at that level. In contrast, sustained release articles dispense an agent at a constant rate and do not display the feedback regulation of release that a controlled release article displays.

It will be appreciated that articles operating by the controlled release mechanism provide substantial advantages over sustained release articles for certain uses. For example, placement of a properly formulated controlled release medicament system in an animal's body cavity in contact with body fluids establishes and maintains an effective concentration of the medicament in the fluids. The system responds to dilution or depletion as additional fluids are secreted, or the medicament is bound to tissue, absorbed, etc., thereby automatically maintaining the concentration of medicament at the proper level.

As disclosed in the application of Laughlin, above, solutions of micelle-forming surfactant compounds can be releasably enclosed in a container comprising a microporous membrane. Articles prepared in this manner are stable and do not suffer osmotic rupture when placed in body cavities in contact with body fluids. Rather, the stable articles provide controlled release of the surfactant into the body fluids. The proper selection of membrane and surfactant provides a means for achieving various biological effects, e.g., antimicrobial activity, spermicidal activity, and the like. Highly preferred articles herein are those operating by the aforesaid controlled release mechanism. However, articles operating by a sustained release mechanism can also be constructed in the manner disclosed herein so that they can be retained in the vagina during intercourse. Accordingly, sustained release articles of the unique construction and shape of the articles herein are fully contemplated by this invention.

Container

Broadly, the present controlled release articles comprise a container or, preferably, multiple containers, in a total article of the construction depicted in the Figures. The containers have a surfactant solution enclosed therein. At least one portion of the container comprises a microporous membrane which permits the controlled release of surfactant monomers into the environment external to the container, but which prevents the transport of the larger surfactant micelles. In short, the membrane acts as a selective "sieve" at the colloidal/molecular level.

Containers used in the present articles can be partly made of any stable material such as glass, plastic, etc., which is not permeable, even to surfactant monomers. Of course, the container should be made from a material which is inert to the biologically active agents being used, but selection of inert container materials is not a problem. At least some portion of the container used in the controlled release articles herein must comprise a microporous membrane to allow controlled release of surfactant monomer into the vaginal cavity. Preferred controlled release articles are those wherein the container comprises an envelope of the membrane.

The membranes used in the controlled release articles are characterized by parameters which reflect their strength, integrity and ability to act as a selective sieve for surfactant monomers, as follows.

The membranes should be substantially water-insoluble so that they maintain their strength and integrity when in contact with body fluids.

The membranes should be of a thickness (wet) less than about 150 microns ($\mu$) and are most preferably about 25–50$\mu$ thick (wet). Membranes thicker than about 150$\mu$ (wet) tend to impede release of surfactant monomer, whereas thicknesses below ca. 5–10$\mu$ (wet) cause the articles to be subject to osmotic rupture even by the relatively low osmotic pressures of the concentrated surfactant solutions used in the articles.

Since the articles are to be used in contact with body fluids and tissues, the membranes (and total container and article) should be toxicologically acceptable. Moreover, the membrane material will most preferably be immunologically acceptable and will not be rejected by the body's natural defense mechanisms nor have any untoward effect on the rate of antibody formation, and the like.

Finally, the membrane most preferably has the ability to act as a "sieve" for the surfactant monomers in order to provide the controlled release benefit of the article. An important consideration in this regard is that the surfactant must not be soluble to any substantial extent in the membrane material. If the surfactant were to be soluble in the membrane material, uncontrolled release would ensue. (Of course, if simple sustained release is desired, other, appropriate, membranous materials can be used.)

The membranes preferably employed herein comprise a solid wall material having multiple miniscule pores therethrough, i.e., are microporous. The pores of the membrane are filled, or substantially filled, with solvent (e.g., water) for the surfactant monomer. In use in the containers of the instant controlled release articles, surfactant monomers migrate from the inner reservoir of micellar monomers migrate from the inner reservoir of micellar surfactant solution to the external environment by means of diffusion through the solvent in these solvent-filled pores, which pores extend from inner to outer surfaces of the articles.

It will be appreciated by those skilled in the art that pore diameters of the membranes herein cannot be specified in absolute terms. Indeed, when dealing with pore sizes at the molecular level (i.e., at the dimensions of surfactant monomers) measurement techniques are only indirect and generally constitute a determination of which molecules (or association colloids) will pass through a given membrane and which will be retained, coupled with approximations of the molecular dimensions of the molecules that do pass.

Based on the foregoing, the pores in the membranes used in the present controlled release articles are characterized by diameters on the order of the size of the surfactant monomers herein, but are smaller than the surfactant micelles (i.e., association colloids comprising ca. 100–1000 monomer units). An experimental Surfactant Transport Procedure for selecting microporous membranes having the appropriate pore size for use in the articles is set forth below.

Membranes suitable for use as the container can be made from any material which possesses the abovedescribed characteristics and properties. For example, suitably perforated polyethylene, polypropylene, polyvinylchloride, etc., sheeting can be used in the present articles.

Preferred membranes herein are prepared from water-swellable polymers such as polyvinyl alcohol (suitably modified so as to be water-insoluble) and cellulose. Cellulose is a highly preferred membrane material, inasmuch as it has a long history of safety when used in prolonged contact with animal tissue. Such swellable polymers (or polymer precursors) can be cast into membranes which swell to about 1.8 to 2.0 times their dry thickness on contact with water. This swelling action automatically opens pores in the polymer membrane, and these pores are of the proper size to permit passage of surfactant monomers, and to prevent passage of surfactant micelles, through the membrane.

Methods for casting swellable cellulose membranes are well known and form no part of this invention. In general terms, a cellulose derivative (e.g., cellulose acetate) is dissolved in a suitable solvent (e.g., acetone) and the solution is spread onto a smooth surface, whereupon the solvent evaporates leaving a continuous film of the cellulose derivative. The film of cellulose derivative is thereafter converted back to cellulose using an aqueous ammonia solution and swollen with water to provide a membrane suitable for use as the container of the present articles.

As will be appreciated from the foregoing, a variety of materials can be used as the membranous container portion of the controlled release articles, with solvent-swellable polymers being the most preferred due to their inherent sub-microscopic porosity in the swollen state. An experimental procedure which can be used to select membranes for use herein is as follows.

Surfactant Transport Procedure

A cell for testing transport of surfactant monomers through membranes is as follows. A 40 mm. (diameter) × 50 mm. (length) polymethylmethacrylate rod is halved and each half is suitably machined to provide cavities 16 mm. (diam.) × 10 mm. (depth), such that the cavities abut when the rod halves are reassembled. Each cavity is provided with two inlet holes for filling and sampling. A brass clamp is used to hold the two cell halves firmly together.

The surfactant transport testing is carried out in the following manner. A 4 cm. diameter disk of the membrane material to be tested is sandwiched between the cell halves, enclosing a 3 mm. glass bead on each side of the membrane to provide stirring. The cell cavities are filled with saline and the inlet holes are sealed with waterproof tape. After equilibrating overnight at 37° C, the saline in one half of the cell is replaced with a solution of known concentration of radiotagged surfactant. The inlet hole is again taped, and the cell is placed in a 37° C bath in a device which allows the cell to be rotated axially at 50 rpm. Periodically, the cell is raised from the bath and the solution in the desired compartment sampled.

A typical procedure using a membrane cut from viscose cellulose dialysis tubing (Matheson Scientific, 18970-20) is as follows. After equilibrating the cell and charging one side with surfactant as above, the cell is maintained in the 37°C bath for varying time periods, after each of which the tape is removed from the inlet holes and 10 microliter ($\mu$l) samples are removed by syringe. The samples are expressed below the surface of 100 $\mu$l of distilled water in a counting vial. In the subsequent scintillation counting, each sample vial is charged with 10 $\mu$l of a solution of 0.8% 2-diphenyloxazole and 0.01% of 1,4-bis-[2-(4-methyl-5-phenyloxazolyl)]-benzene in a 1:1 ethanol/toluene mixture. The vials (one for each time period) are then placed in the refrigerator compartment of a counting instrument and cooled to 4° C before being counted for 5 minutes each. The counts per minute are converted to ppm by applying a factor found by counting one or more standard samples. By taking samples at regular intervals, a curve plotting the surfactant concentration in the initially surfactant-free side of the cell versus the time of sampling can be drawn which describes the transport of the surfactant across the membrane.

Following the Surfactant Transport Procedure set forth hereinabove, the cell cavity designated (A) is charged with surfactant solution and the cavity designated (B) is charged with saline. The cell, whose cavities are separated by the test membrane, e.g., swollen, microporous cellulose dialysis tubing (dry thickness 25$\mu$; swollen thickness 50$\mu$) is then equilibrated in the indicated manner. The concentration of surfactant transported to cavity (B) is determined in the foregoing manner, and the graph of the concentration of surfactant in (B) v. time is plotted.

A plot of the concentration (B) as the ordinate and time ($t$) as the abscissa describes a monomer transport curve which rises sharply at the outset, and which gradually flattens. The slope of the sharply rising portion of the curve (i.e., over the first five hours of surfactant monomer transport) is the primary slope, $S_1$, and that of the flattened portion of the curve (i.e., 20 hours, and longer, of monomer transport) is the secondary slope, $S_2$.

To achieve the highly desirable and preferred controlled release feature of the articles of the present type, the combination of surfactant and membrane should yield a monomer transport curve wherein $S_1$, i.e., $$\frac{d[B]}{dt}; t = 0 \rightarrow 5 \text{ hrs.}$$

is reasonably steep, and $S_2$, i.e., $$\frac{d[B]}{dt}; t > 20 \text{ hrs.}$$

is reasonably flat, ideally zero. The intercept at zero time of the secondary transport data, having slope $S_2$, should be about equal to the cmc of the surfactant being tested. The ratio of $S_2/S_1$ is from 0 to about 0.1. $S_1$ should be no less than about $50 \times 10^{-6}$ moles $l^{-1}$ hr.$^{-1}$, and preferably should be in the range of about $200 \times 10^{-6}$ moles $l^{-1}$ hr.$^{-1}$ to about $750 \times 10^{-6}$ moles $l^{-1}$ hr.$^{-1}$.

Based on the foregoing, surfactant/membrane combinations can be selected which will provide the controlled release feature in preferred articles of the present type. A highly preferred article which is particularly useful as a controlled release vaginal contraceptive comprises from about a 5 to about a 50% (wt.) aqueous solution of a nonionic surfactant (especially $C_{10}EO_5$, described more fully hereinafter) enclosed within a microporous, swollen cellulose membrane (dry thickness ca. $25\mu$; swollen thickness ca. $50\mu$).

Surfactant

The use of micelle-forming surfactant solutions to provide the controlled release feature of the present contraceptive articles results in several important advantages over other types of metered dosage systems.

The use of spermicidal micelle-forming surfactants as the controlled release active agent maintains the osmotic pressure in the containers at a relatively low level. (The terms "spermicide" and "spermicidal" as employed herein are intended to encompass agents which truly "kill" animal sperm as well as those which immobilize or otherwise render sperm cells inactive.) Accordingly, the pressure differential across the enclosing container is relatively small, and the container is stable and does not rupture. This desirable attribute of the present articles is to be contrasted with the situation which occurs when a similarly concentrated solution of a non-micelle-forming solute of similiar molecular weight is enclosed by a diffusion membrane, whereupon osmotic pressures of tens or hundreds of atmospheres can be developed, thereby leading to rupture of the membrane.

Moreover, the surfactants employed as the controlled release active agent of the contraceptive articles of the present invention appear to function by an entirely localized effect on motile sperm. Accordingly, undesirable side-effects which can accompany the prolonged use of systemic contraceptive drugs such as hormones are avoided.

In addition, the use of safe, effective surfactants as the controlled release spermicide permits the formulator of the articles to employ a large excess of the spermicide therewith. The controlled release feature allows formulation of articles containing more spermicide than the usual expected need but (1) reduces the probability of side-effects by regulating the concentration to a maximum level, and (2) allows for unusual variations in the amount of compound required or in the time period over which it might be needed. Accordingly, a "safety factor" of the order of 1000-fold vis-a-vis prolonged contraceptive efficacy is provided by the articles.

The surfactants employed in the instant articles and processes are characterized by several parameters. In general, the surfactants are selected from those which, in combination with the microporous membrane described hereinabove, provide an appropriate relationship between release and the desired contraceptive end use of the article.

The surfactants herein are characterized by their ability to dissolve in a solvent (normally water) and to form an association colloid therein. The grossly anomalous (low) osmotic pressures displayed by concentrated solutions of the surfactants herein are attributable to the association of surfactant monomers into micellar structures. This phenomenon is of considerable practical significance in that it allows fabrication of articles containing surfactants at extraordinarily high concentrations, as compared with concentrations permitted with other, non-associative types of solutes, without osmotic rupture of the enclosing membrane. In order to realize fully the unique advantages of surfactants in this regard, it is preferred to use those surfactants having a cmc of at most about $1 \times 10^{-3}$ molar (M).

When intended for use as between-period contraceptives (or to provide other desirable effects such as the controlled release of antimicrobial surfactants), it is, of course, necessary to select surfactants which produce the desired biological response. Moreover, to secure the benefits of controlled release, it is necessary also to select surfactants whose monomers are rapidly transported through the diffusion membrane to establish an effective concentration of surfactant in the medium external to the article.

From the foregoing considerations it will be appreciated that the desired biological response of a surfactant can be tested in vitro in a medium (such as physiological saline, which closely approximates various body fluids) to determine the concentration at which the surfactant must be present in such medium to provide the desired response (e.g., spermicidal efficacy). Surfactants whose monomers are transported through the enclosing membrane of the article to provide at least the aforesaid effective concentration in the saline are useful herein. Over a given time period, the controlled release articles herein produce a stable maximum (or "plateau") concentration of surfactant in the external fluids. The magnitude of this plateau concentration is related to the cmc of the surfactant compound, and is approximately equal to the cmc. It follows that, for the desired effect to be realized, the ratio, R, of the *cmc* of the surfactant to its biologically effective concentration, $C_{biol.}$, in saline, i.e., $$R = \frac{cmc}{C_{biol.}}$$

must be greater than about 1. Similar considerations hold for external media other than saline, i.e., fluid media such as body fluids, water, etc., in which the present surfactant monomers are soluble. Accordingly, the preferred compounds for use in the articles described herein have values of R which are > ca. 1, i.e., $$R > ca. 1.$$

A variety of surfactants exhibit a *cmc* less than the requisite about $10^{-3}$M and meet this criteria for use in the present controlled release articles. Moreover, several surfactant types having the requisite *cmc* provide desirable biological responses, e.g., microbiocidal or static activity and/or spermicidal activity. Moreover, several surfactants exhibit the requisite relationship, $R > ca. 1$, between *cmc* and biological activity.

Based solely on the foregoing considerations, representative examples of surfactants useful herein include nonionic surfactants such as $C_{10}H_{21}(OCH_2CH_2)_5OH$ (abb. $C_{10}EO_5$) and $C_{10}H_{21}(OCH_2CH_2)_6OH$ ($C_{10}EO_6$); semipolar surfactants such as $C_{12}H_{25}S(NH)_2CH_3$ and $C_{12}H_{25}(CH_3)_2AsO$; and cationic surfactants such as $C_{16}H_{33}N^+(CH_3)_3,Cl^-$ and $C_{16}H_{33}N^+C_5H_5,Cl^-$. These surfactants are characterized by $R \gtrless 2$ and $cmc < 10^{-3}$M.

It is to be understood that other surfactants having the requisite *cmc* of $10^{-3}$M, or less, but which exhibit lower biological activity (especially as spermicidal agents), i.e., surfactants wherein $ca. 1 > R > 2$, can be employed in controlled release articles. However, the biological response to these latter surfactants is somewhat less than that of the preferred group, and the efficacy margin, i.e., R-1, is not as great. Included among this group of surfactants are $C_{12}EO_9$; $C_{16}EO_1.SO_4^-,Na^+$; $C_{12}(CH_3)_2PO$; $C_{10}EO_4$; $C_{12}(C_2H_5)_2PO$; $C_{16}$ ammoniopropanesulfonate; $\beta-OCH_{12}(CH_3)_2PO$; and nonylphenol nonaethoxylate.

As can be seen from the foregoing, various surfactant types are useful in the controlled release articles herein. However, when articles designed for use as between-period contraceptives are being prepared, additional physio-chemical properties of the surfactants must be considered. For example, the surfactants should be toxicologically acceptable for use in the body over extended time periods. The surfactants should also be non-irritating to the delicate tissues of the vagina and uterus. The preferred surfactants should not substantially bind serum proteins found in the vaginal area between periods of menstrual flow, inasmuch as the bound surfactant-protein moiety does not function as a spermicide and accelerates the depletion of surfactant from the reservoir within the article. Finally, the surfactant should be selected from those which do not bind to ionically charged sites in the enclosing diffusion membrane, since binding leads to unregulated transport through the membrane.

Based on the foregoing factors, and considering the high spermicidal activity of the compounds, the $C_{10}EO_5$ and $C_{10}EO_6$ surfactants are most preferred for use in the present controlled release contraceptive articles. As between these latter compounds, $C_{10}EO_5$ has the advantage of the lower molecular weight, and therefore provides more monomer per given weight of compound. Accordingly, $C_{10}EO_5$ is most preferred for use in the between-period, controlled release contraceptive articles of this invention.

The surfactants disclosed hereinabove are all well known from the detergency arts and can be made by various art-disclosed processes.

Article Construction

Sheets of cellulose acetate (CA) film are cast from acetone solutions of a suitable CA resin, e.g., Eastman Kodak E-394, and plasticizer, e.g., triethyl citrate, to a thickness as disclosed hereinabove. (Preferred plasticizer content is about 20% by weight based on the finished film.)

The film sheets are then thermoformed into appropriate film pieces used to assemble containers of the shape depicted in the Figures using standard thermoforming procedures. In the thermoforming process, the film is radiantly heated and then pulled by vacuum into a die.

A solution of the active agent (e.g., the nonionic surfactant spermicide) is then charged into each thermoformed film piece. The concentration of the active solution should be about 2×–4× the concentration desired in the finished article. A volume of solution is used which will provide the weight of active material desired in the finished article. (A smaller volume than that needed to fill the containers is conveniently used to prevent the solution from flowing onto the film edges, since the presence of the solution on the film edges could prevent sealing.) After charging the thermoformed film piece, a cover sheet (either flat or appropriately thermoformed into a desired bubble shape) is solvent sealed (or, alternatively, heat sealed) to the first thermoformed film piece which is charged with the solution of active agent. Sealed, charged finished containers are formed thereby.

Sealed units are then formed into the ring shape depicted in the Figures by connecting two ends of a straight piece using a solvent- or heat-sealed tab.

The sealed containers are then immersed in a ca. 4 molar aqueous ammonia solution containing 10% by weight sodium chloride at a temperature of 50° C–60° C. The foregoing treatment deacetylates the CA film, thereby converting the CA container to a cellulose container. The completeness of the deacetylation reaction can be monitored spectrophotometrically using the "carbonyl peaks" (1740 cm.$^{-1}$).

When deacetylation is complete, or substantially so, the container with the active is transferred to a bath containing the same solvent (usually water) used in the charging step, whereupon the container fills with solvent due to osmotic effects. During filling, the originally charged, concentrated solution is diluted to the final, desired concentration of active.

The following examples illustrate the articles of this invention and their use, but are not intended to be limiting of the invention herein.

EXAMPLE I

Figure 1:
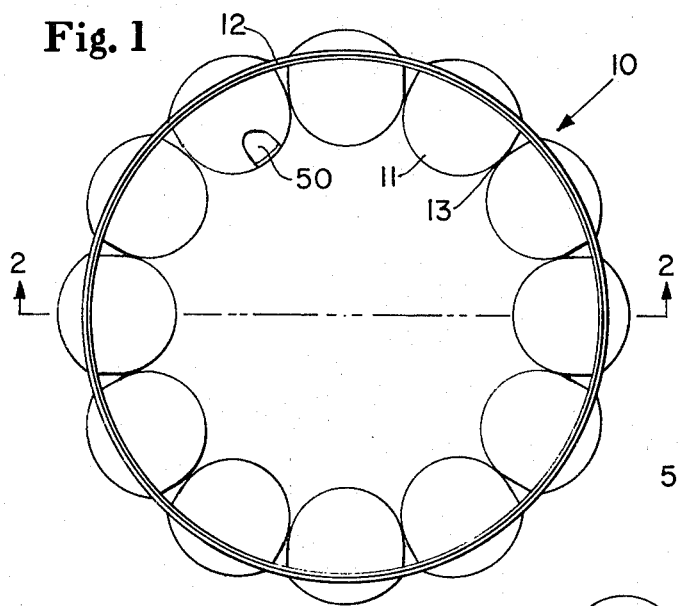
FIG. 1 is a plan view of an article 10 of the present type. The article comprises multiple containers 11 held in place by a flexible seal fin 12 which is in the plane substantially perpendicular to the plane of the article. Containers 11 abut at points 13, thereby holding the flexible article in a substantially circular configuration.

An article of the type depicted in FIG. 1 is prepared from cellulose acetate using the thermoforming methods described hereinabove. The article comprises 16 separate containers, each of which is *ca.* 9 mm. in diameter. The overall article has an outside diameter of *ca.*

54 mm. and an inside diameter of ca. 37 mm. and is in a substantially ring structure as depicted in FIG. 1.

An article of this type wherein the containers are substantially filled with the $C_{10}EO_5$ surfactant and wherein the article is deacetylated in the manner described above is ready for use as a vaginal contraceptive. An article of this type exhibits a monomer transport curve with $S_2/S_1$ of ca. 0.

The article is placed in the vagina posterior to the introitus. The article is worn during the time between menses and safely delivers a spermicidally effective amount of the $C_{10}EO_5$ surfactant to the vaginal area. The article can remain in place during intercourse.

In the article of Example I, the $C_{10}EO_5$ surfactant is replaced by an equivalent amount of $C_{10}EO_6$ surfactant and excellent spermicidal results are secured.

An article of the type depicted in FIG. 3 is prepared. The individual containers are ca. 9 mm. in diameter and are substantially filled with an aqueous solution of a $C_{10}EO_5$ surfactant. However, the seal fin is so disposed in the article that there is no substantial contact between the containers. The article does not assume a substantially ring shape and is not satisfactorily retained within the vagina.

In the article of Example I the $C_{10}EO_5$ surfactant is replaced by an equivalent amount of the following surfactants, respectively: 1:1 (wt.) $C_{10}EO_5$ and $C_{10}EO_6$; $C_{16}H_{33}N^+(CH_3)_3,Cl^-$; $C_{16}H_{33}N^+C_5H_5,Cl^-$; and $C_{12}H_{25}S(NH)_2CH_3$. On insertion of the article in the vaginal cavity, these surfactants are released over a prolonged period of time.

EXAMPLE II

Cellulose acetate (Eastman Kodak E-394) is cast into a film sheet having a dry thickness of ca. $20\mu$. The cellulose acetate film sheet is thermoformed to provide parallel rows of hemispherical containers, said containers being ca. 9 mm. in diameter and ca. 6 mm. apart. The cellulose acetate film sheets are trimmed into strips, ca. 15 mm. in diameter.

The hemispherical containers are filled to two-thirds their volume with a ca. 30% (wt.) aqueous solution of $C_{10}EO_5$ surfactant. A second film strip with multiple hemispherical indentations is superposed over the first, and the strips are solvent-sealed together with acetone, thereby providing a strip of spherical containers charged with the surfactant solution. A portion of the film strip comprising 13 charged containers is folded, joined at the ends in a ring configuration and solvent-sealed with acetone.

The surfactant-charged strip of the foregoing type is deacetylated by submersion in a 4 M aqueous ammonia solution containing 10% (wt.) sodium chloride at a temperature of 50° C for 4 hours. This treatment converts the cellulose acetate containers to cellulose.

When deacetylation is complete, the surfactant-charged film strip is transferred to a water bath, whereupon the containers fill and swell to provide a final concentration of surfactant of ca. 10%. The swollen containers abut and hold the article in a ring shape.

The article prepared in the foregoing manner is substantially that depicted in FIG. 5 herein.

The article of the foregoing type is folded and placed in the vagina posterior to the introitus. The article resumes a substantially ring shape. The article is worn during the time between menses and safely delivery a spermicidally effective amount of the $C_{10}EO_5$ surfactant to the vaginal area for a period of 28 days. The article can remain in place during intercourse.

What is claimed is:

1. An article for use within the vaginal cavity characterized by: a plurality of containers, said containers having walls releasably containing a biologically active agent, said containers being connected by a thin, flexible seal fin in the plane perpendicular to the plane of the article defining a means for holding said article in a substantially circular configuration comprising adjacent containers being carried by said fin in such manner as to provide points of abutment between adjacent containers.

2. A controlled release article according to claim 1 especially adapted to maintaining a useful concentration of a biologically active surfactant compound in the vaginal cavity, wherein at least a portion of the walls of said containers comprise a microporous membrane, and wherein said containers are substantially filled with a biologically active agent consisting essentially of an aqueous solution of a micelle-forming surfactant compound, said solution having a concentration above the critical micelle concentration of the surfactant compound.

3. An article according to claim 2 wherein the containers comprise cellulose.

4. An article according to claim 3 wherein the surfactant compound is characterized by a critical micelle concentration of at most about $1 \times 10^{-3}$ Molar.

5. An article according to claim 4 wherein the combination of surfactant and cellulose membrane exhibits a monomer transport curve having a ratio of slopes $S_2/S_1$ in the range of 0 to about 0.1.

6. An article according to claim 5 wherein the surfactant has an R value greater than 1.

7. An article according to claim 6 wherein the surfactant is a biocidal or biostatic agent.

8. A contraceptive article according to claim 7 wherein the surfactant is a member selected from the group consisting of spermicidal surfactants.

9. A contraceptive article according to claim 8 wherein the surfactant is a nonionic surfactant selected from ethylene oxide condensates of aliphatic alcohols.

10. A contraceptive article according to claim 9 wherein the nonionic surfactant is $C_{10}EO_5$.

11. A contraceptive article according to claim 9 wherein the nonionic surfactant is $C_{10}EO_6$.

12. A contraceptive article according to claim 9 wherein the nonionic surfactant is selected from $C_{10}EO_5$ or $C_{10}EO_6$, or mixtures thereof, and the containers comprise waterswollen microporous cellulose having a dry thickness of ca. $5-25\mu$ and a swollen thickness of ca. $10-50\mu$.

* * * * *